United States Patent
Bornzin et al.

(10) Patent No.: US 10,292,621 B2
(45) Date of Patent: May 21, 2019

(54) SYSTEMS AND METHODS FOR RETRIEVING AN IMPLANTABLE DEVICE

(71) Applicant: PACESETTER, INC., Sylmar, CA (US)

(72) Inventors: Gene A. Bornzin, Simi Valley, CA (US); Didier Theret, Porter Ranch, CA (US); Zoltan Somogyi, Simi Valley, CA (US)

(73) Assignee: PACESETTER, INC., Sylmar, CA (US)

( * ) Notice: Subject to any disclaimer, the term of this patent is extended or adjusted under 35 U.S.C. 154(b) by 505 days.

(21) Appl. No.: 15/050,896

(22) Filed: Feb. 23, 2016

(65) Prior Publication Data

US 2017/0065369 A1    Mar. 9, 2017

Related U.S. Application Data

(60) Provisional application No. 62/215,622, filed on Sep. 8, 2015.

(51) Int. Cl.
| | |
|---|---|
| *A61N 1/00* | (2006.01) |
| *A61B 5/06* | (2006.01) |
| *A61B 5/00* | (2006.01) |
| *A61B 5/04* | (2006.01) |
| *A61B 5/042* | (2006.01) |
| *A61B 90/00* | (2016.01) |

(52) U.S. Cl.
CPC .............. *A61B 5/062* (2013.01); *A61B 5/686* (2013.01); *A61B 5/042* (2013.01); *A61B 2090/3954* (2016.02); *A61B 2562/0223* (2013.01)

(58) Field of Classification Search
USPC ............... 600/372–375, 377, 391, 393, 407, 600/409–411, 422–424, 431, 433–435, 600/508–518; 607/1–5, 7, 119, 132, 116, 607/125
See application file for complete search history.

(56) References Cited

U.S. PATENT DOCUMENTS

| | | | | |
|---|---|---|---|---|
| 5,312,439 | A * | 5/1994 | Loeb | A61N 1/04 607/1 |
| 6,735,475 | B1 * | 5/2004 | Whitehurst | A61N 1/08 607/46 |
| 7,822,484 | B1 * | 10/2010 | Zhao | A61N 1/056 600/375 |
| 2005/0057905 | A1 * | 3/2005 | He | A61N 1/3605 361/760 |
| 2005/0267555 | A1 * | 12/2005 | Marnfeldt | A61B 17/3417 607/116 |
| 2012/0165827 | A1 * | 6/2012 | Khairkhahan | A61N 1/362 606/129 |
| 2013/0116740 | A1 * | 5/2013 | Bornzin | A61N 1/3756 607/9 |

* cited by examiner

*Primary Examiner* — Joseph A Stoklosa
*Assistant Examiner* — Brian M Antiskay

(57) ABSTRACT

The present disclosure provides systems and methods for retrieving an implantable device. An implantable device includes a casing, and a marker coupled to the casing, wherein the marker includes a detectable material encased in a biocompatible material, and wherein the marker facilitates accurately locating and retrieving the implantable device after implantation in a patient.

16 Claims, 6 Drawing Sheets

SYSTEMS AND METHODS FOR RETRIEVING AN IMPLANTABLE DEVICE

CROSS REFERENCE TO RELATED APPLICATIONS

This application claims the benefit of U.S. Provisional Application Ser. No. 62/215,622, filed Sep. 8, 2015.

FIELD OF THE DISCLOSURE

The present disclosure relates generally to implantable cardiac monitors (ICMs), and more particularly to systems and methods for implanting ICMs.

BACKGROUND ART

Implantable cardiac monitors (ICMs) are devices that may be implanted under a patient's skin to continuously monitor the patient's cardiac activity. An ICM may be programmed to detect and record cardiac information and episodes such as atrial/ventricular tachycardia, atrial fibrillation, bradycardia, asystole, etc. Triggers for detecting and recording an event (e.g., such as a tachy/brady detection rate, a number of events, and/or a duration of asystole) may be programmed by a clinician. Alternatively, when the patient experiences symptoms, the patient may activate the detection and recording using an external patient activator. Diagnostics and recorded events may be downloaded by the clinician in-clinic using a programmer. Further, the data may also be transmitted to the clinician using a daily remote monitoring system.

ICMs are generally relatively small (e.g., 1.1-1.5 $cm^3$ in volume), and can be implanted using a relatively small incision (e.g., 1 cm). Once inserted under the patient's skin, the ICM has a relatively slim profile, mitigating patient concerns about body image. The ICM may be implanted in the patient's chest area near the sternum, and the implant procedure may take less than 10 minutes after application of a local topical anesthesia. Further, ICMs do not deliver pacing or shock therapies to the patient, nor do they require leads to be implanted in the patient's heart.

After a period of time, implanted devices, such as an ICM, may need to be retrieved from a patient. For example, an implanted device may be retrieved if a battery of the device fails, a diagnosis performed using the device is complete, or the device is causing an infection. An implanted device may also be retrieved for cosmetic purposes. Notably, in at least some known systems, given the size of the implantable device, it may be relatively difficult to locate and retrieve the device. For example, in at least some known systems, a physician takes x-rays of the patient in an attempt to determine a generation location of the device, makes an incision (which may or may not be proximate the device) based on the x-rays, and attempts to grab and remove the device.

BRIEF SUMMARY OF THE DISCLOSURE

In one embodiment, the present disclosure is directed to an implantable device. The implantable device includes a casing, and a marker coupled to the casing, wherein the marker includes a detectable material encased in a biocompatible material, and wherein the marker facilitates accurately locating and retrieving the implantable device after implantation in a patient.

In another embodiment, the present disclosure is directed to an implantation system. The implantation system includes an implantable device including a casing, and a marker coupled to the casing, wherein the marker includes a detectable material encased in a biocompatible material, and wherein the marker facilitates accurately locating and retrieving the implantable device after implantation in a patient. The implantation system further includes an insertion tool configured to implant the implantable device in the patient.

In another embodiment, the present disclosure is directed to a method for retrieving an implanted device from a patient. The method includes locating a marker included within the implanted device by detecting a detectable material encased in a biocompatible material and included within the marker, making an incision in skin of the patient proximate the located marker, and retrieving the implanted device through the incision.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for retrieving an implanted device. An implantable device includes a casing, and a marker coupled to the casing, wherein the marker includes a detectable material encased in a biocompatible material. Once implanted, the marker can be detected to facilitate locating and retrieving the device.

The systems and methods described herein facilitate retrieving relatively small injectable devices that have previously been implanted in a patient. Injectable devices that are retrievable using the systems and methods described herein may include, for example, an implantable cardiac monitor (ICM), a birth control device, and a leadless pacemaker. Although embodiments directed to an ICM are described herein in detail, those of skill in the art will appreciate that similar systems and methods may be implemented for retrieving other types of injectable devices.

At least some embodiments described herein include a marker attached to an injectable device (e.g., with a suture) and positionable just under the skin of the patient. A dilator and/or other insertion tool may be used to inject the device. A device finder allows a physician to locate the injectable device and mark the location of the injectable device on the skin of the patient. Once the injectable device is located, the skin just over the marker may be cut, and a tool (e.g., a hemostat) may be used to retrieve the injectable device. In some embodiments, a suture is coupled to the marker, and a dilator may be used to follow the suture and create a tunnel to the injectable device, such that the suture can then be pulled to retrieve the device through the tunnel.

Figure 1:
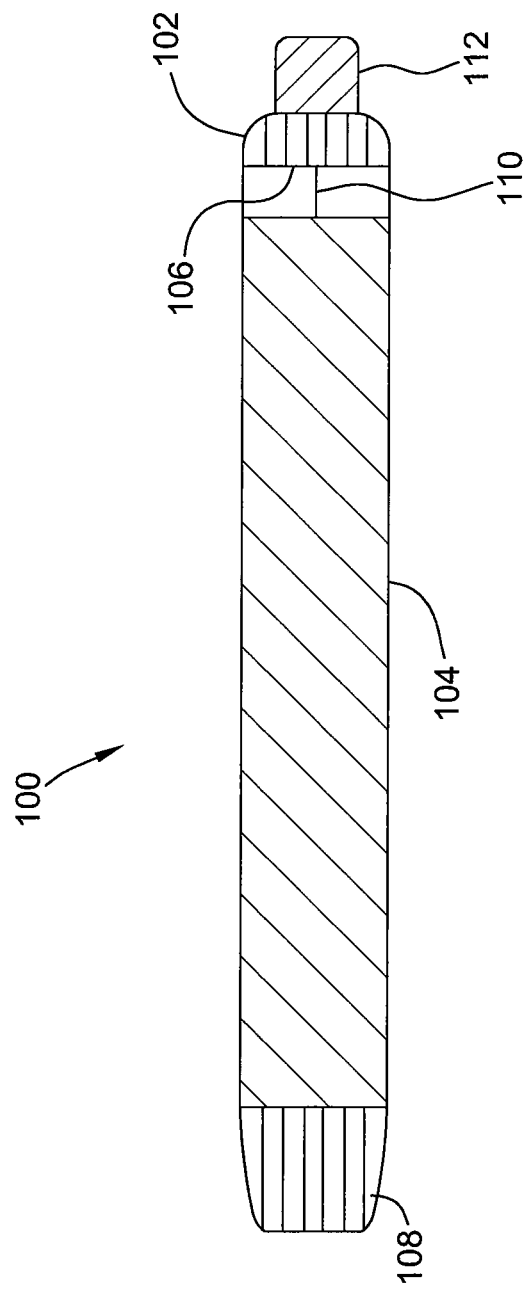
FIG. 1 is a schematic diagram of one embodiment of an implantable cardiac monitor (ICM).

Referring now to the drawings and in particular to FIG. 1, an implantable cardiac monitor (ICM) is indicated generally at 100. ICM 100 includes a proximal pickup electrode 102 that may be made of a biocompatible metal (BCM), such as titanium, 304 stainless steel, or 316 stainless steel. Proximal pickup electrode 102 is attached to a casing 104 using a suitable epoxy 106. Casing 104 may also be made of a BCM. For operation of ICM 100, in this embodiment, casing 104 includes circuitry, a battery, and a receiving and transmitting antenna. Casing 104 is insulated with a coating (e.g., a parylene coating) with the exception of a distal portion 108. Distal portion 108 functions as a counter electrode to proximal pickup electrode 102 for detecting electrocardiograms. Proximal pickup electrode 102 is connected to circuitry in casing 104 using a feedthrough pin 110, as will be understood by those of skill in the art.

In this embodiment, ICM 100 includes a marker 112 that couples to proximal pickup electrode 102. For example, marker 112 may engage proximal pickup electrode 102 in a snap-fit configuration. Marker 112 may also be tied to proximal pickup electrode 102 using a suture (not shown in FIG. 1), as described below. Marker 112 is a BCM at least partially filled with a detectable material in this embodiment. The detectable material may include, for example, a ferrous material such as soft iron, or a permanent magnet made of sintered neodymium-iron-boron or a similar material. The permanent magnet is protected from body fluids because marker 112 encloses the permanent magnet in a BCM housing.

Because marker 112 includes the detectable material, marker 112 can be detected, and thus located, under the skin of a patient. For example, if marker 112 is filled with soft iron, a miniature metal detector with a loop coil having a diameter of approximately 1-2 centimeters (cm) or less may be used to locate marker 112 below a surface of the skin. Metal detectors are well-known and operate by detecting a small shift in a resonant frequency of a circuit that includes a loop coil, the shift caused by proximity of a material (e.g., soft iron) that alters an inductance of the loop coil.

If marker 112 includes a permanent magnet, a giant magnetoresistance (GMR) sensor may be used to locate the permanent magnet, and thus marker 112, under the skin. The larger the magnetic field detected by the GMR sensor, the closer the GMR sensor to marker 112.

Figure 2:
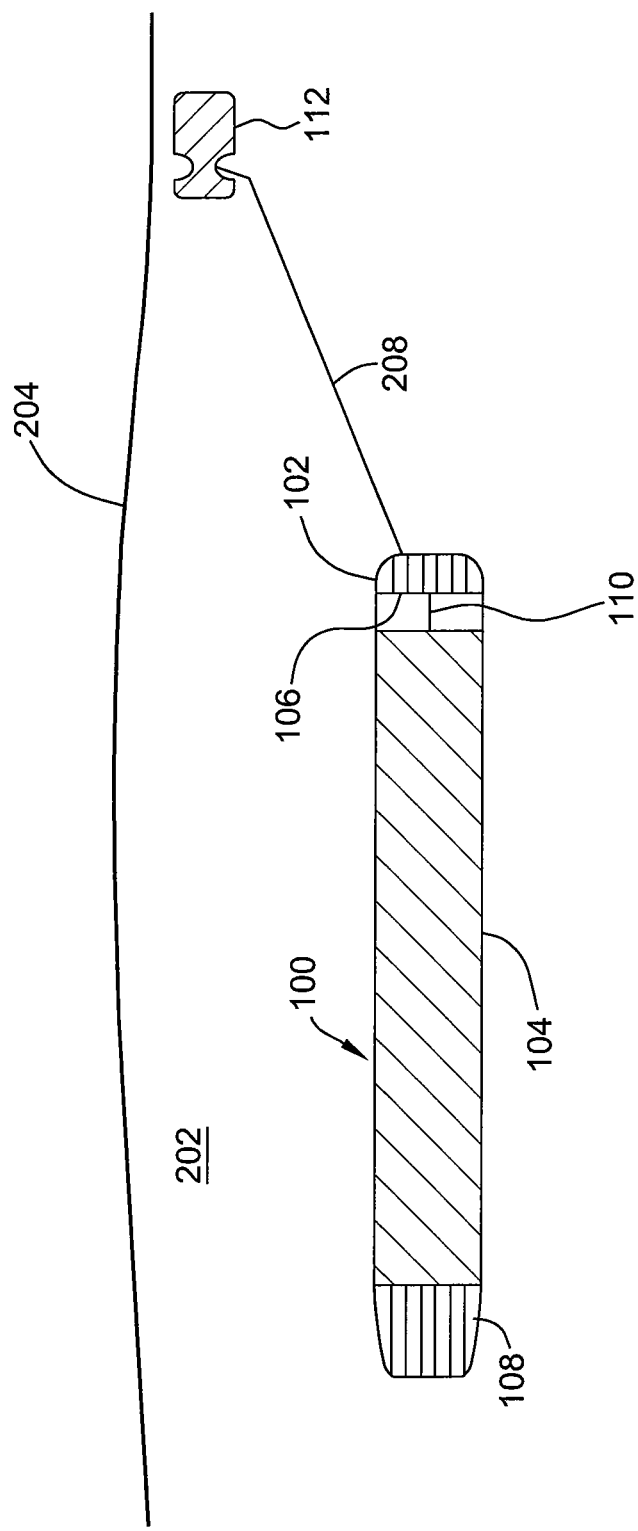
FIG. 2 is a schematic diagram of the ICM shown in FIG. 1 implanted in a patient.

FIG. 2 is a schematic diagram of ICM 100 implanted in tissue 202, below the skin 204 of a patient. As shown in FIG. 2, ICM 100 is implanted relatively deep beneath skin 204, but marker 112 has disengaged from proximal pickup electrode 102 (i.e., from a snap-fit engagement). However, marker 112 is still connected to proximal pickup electrode 102 via a suture 208. Further, marker 112 is relatively near the surface of skin 204. Depending on what material marker 112 includes, marker 112 may be located, for example, using a metal detector or GMR sensor, as described above.

Once marker 112 is located, a small incision (e.g., 3 millimeters (mm)) may be made in skin 204, and marker 112 may be grabbed (e.g., using a hemostat) and pulled through the incision. In this embodiment, suture 208 may be a high tensile strength non-absorbable material suture that has a pull tensile strength of approximately a 5 kilogram (kg) force. Alternatively, suture 208 may have any suitable composition and/or properties. Once marker 112 is pulled through the incision, suture 208 can be pulled on (e.g., using a hemostat) to extract ICM 100 from the patient through the incision. The incision is then closed (e.g., using a tissue adhesive).

In some embodiments, marker 112 includes a material such as soft iron or an encapsulated permanent magnet (e.g., a neodymium magnet), such that the person explanting marker 112 may simply sweep the skin above the implant site using a strong permanent magnet (e.g., a neodymium magnet). When the explanter feels a force on the sweeping magnet, the explanter knows the sweeping magnet is near marker 112. If marker 112 incorporates a permanent magnet, then the explanter may simply sweep above the expected implant area with a ferromagnetic material such as soft iron. Again, the marker will cause a force to be exerted on the ferromagnetic material, but the force may not be as strong as when using a permanent magnet as the sweeping magnet. In yet another embodiment, marker 112 is made of a simple ferromagnetic material (i.e., not a permanent magnet), and the sweeper magnet may be a strong permanent magnet.

In some instances, ICM 100 may be not be easily extracted by pulling on suture 208. Accordingly, in such circumstances, a suture extension (not shown) may be tied to suture 208 and threaded through a dilator. The dilator can then be used to push through the tissue 202 along the path of suture 208, creating a channel or path through tissue 202 to ICM 100. Once the channel is established, ICM 100 may be easily extracted by applying a relatively slight pull to suture 208.

Figure 3:
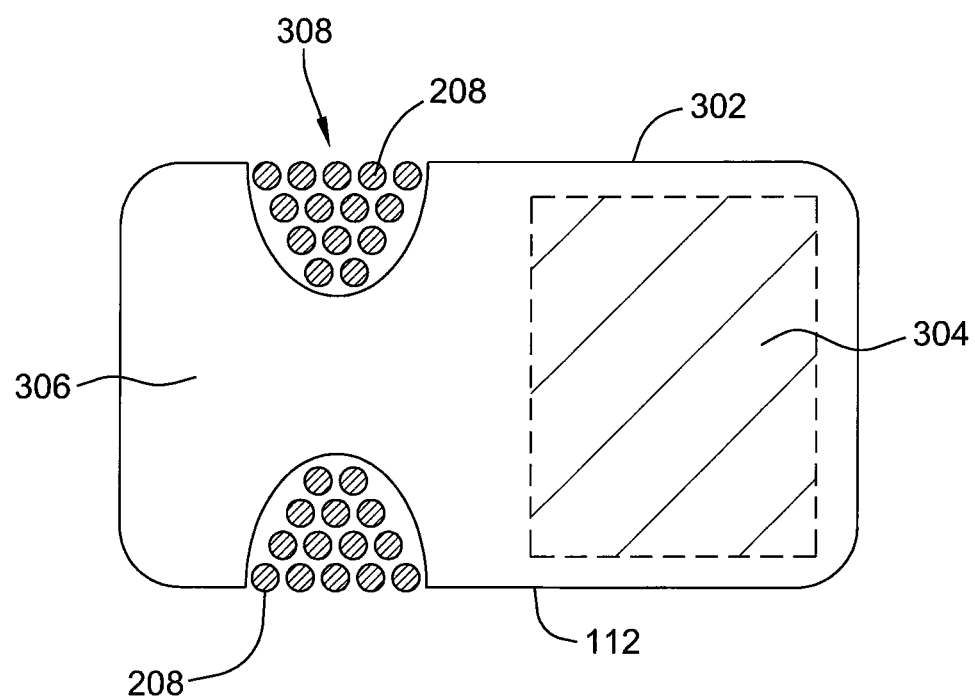
FIG. 3 is a schematic diagram of one embodiment of a marker that may be used with the ICM shown in FIG. 1.

FIG. 3 is a schematic diagram of marker 112. As described above, marker 112 is encapsulated by a BCM 302 and includes a detectable material 304 therein (e.g., a ferrous metal or a permanent magnet). As shown in FIG. 3, in this embodiment, marker 112 includes a bobbin portion 306 that defines an annular recess 308. To couple marker 112 to suture 208, suture 208 may be coiled around or tied to bobbin portion 306. Bobbin portion 306 may be shaped to engage proximal pickup electrode 102 (e.g., in a snap-fit engagement).

FIGS. 4A-4D are schematic diagrams of operation of a system 400 for implanting ICM 100. Specifically, system 400 includes ICM 100 and an insertion tool 401. Insertion tool 401 includes an injector housing 402 and an obturator 404. Injector housing 402 includes a substantially cylindrical tube 408 that extends from a first end 410 to a second end 412. Tube 408 includes a first tube portion 414 proximate first end 410 and a second tube portion 416 proximate second end 412. In the illustrated embodiment, first tube portion 414 has an inner diameter that is slightly smaller than an inner diameter of second tube portion 416. Alternatively, first and second tube portions 414 and 416 may have substantially the same inner diameter. Both first and second tube portions 414 and 416 have inner diameters that are larger than a diameter of ICM 100, such that ICM 100 is positionable within tube 408, as described in detail herein. Second end 412 includes an opening 417 to facilitate inserting obturator 404 into injector housing 402. Injector housing 402 includes another opening 418 at first end 410 to facilitate discharging ICM 100 from injector housing 402 into the patient.

In some embodiments, injector housing 402 includes an indicator (not shown), such as a colored band, proximate first end 410. The indicator facilitates aligning injector housing 402 during an implantation procedure, as described herein. Injector housing 402 may be fabricated from, for example, polycarbonate, polysulfone, or another similarly resilient material.

Figure 4:
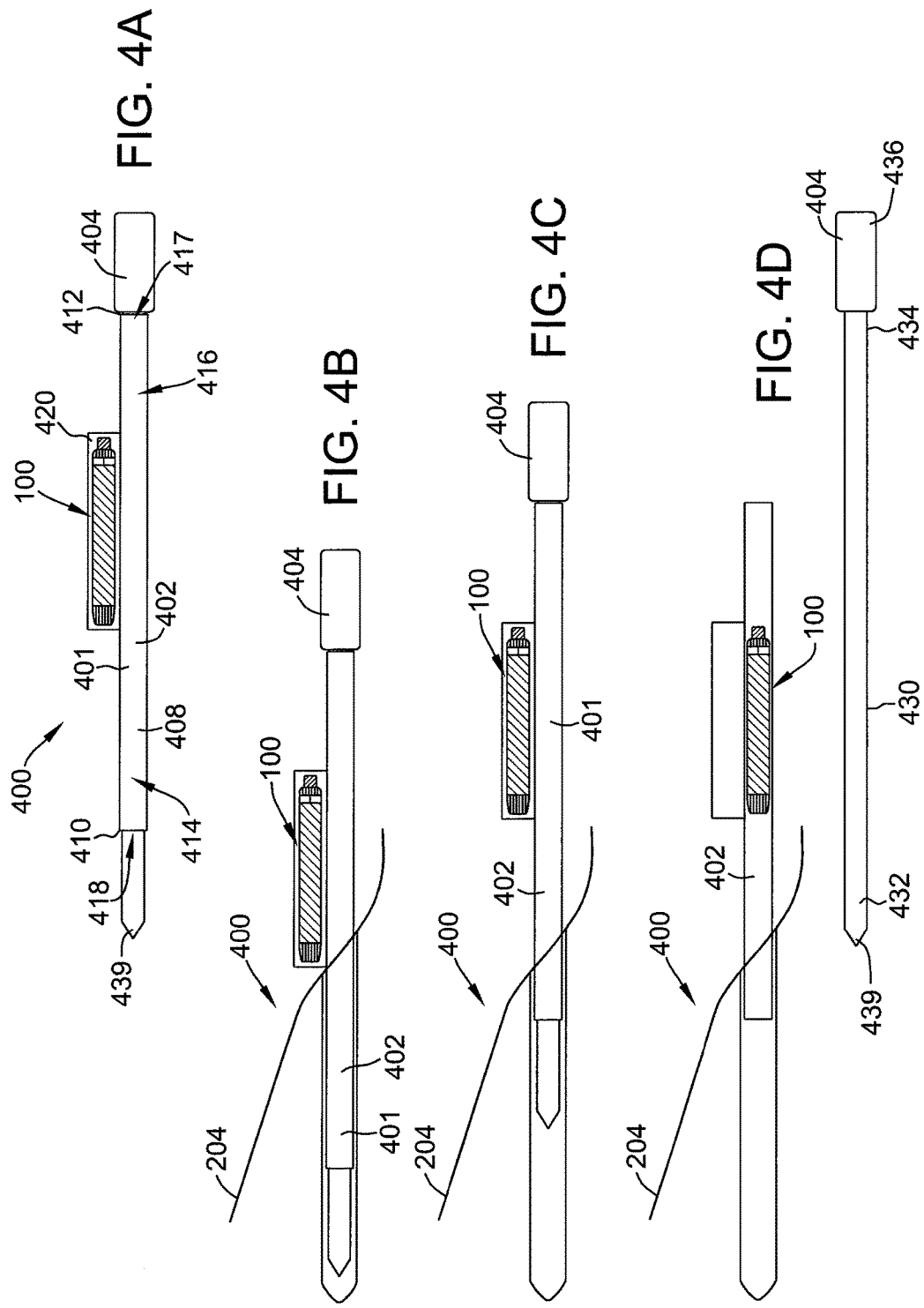
FIGS. 4A-4D are schematic diagrams illustrating operation of one embodiment of a system for implanting the ICM shown in FIG. 1.

Injector housing 402 further includes a receptacle 420 in communication with second tube portion 416 and in communication with the external environment. As shown in FIG. 4A receptacle 420 is sized to receive ICM 100. In the illustrated embodiment, receptacle 420 includes one or more projections that facilitate preventing ICM 100 from falling out of receptacle 420 into the external environment. For example, the projections may engage ICM 100 in a snap-fit engagement to facilitate maintaining ICM 100 in receptacle 420. As shown in FIG. 4A, when ICM 100 is inserted into receptacle 420, obturator 404 is already inserted into first and second tube portions 414 and 416. Accordingly, obturator 404 initially prevents ICM 100 from entering second tube portion 416.

Obturator 404 includes a substantially cylindrical shaft 430 that extends from a first end 432 to proximate a second end 434. An obturator handle 436 is formed at second end 434 of obturator 404. Obturator handle 436 has a diameter that is larger than the diameter of cylindrical shaft 430 and the inner diameter of second tube portion 416. A tip 439 is formed at first end 432 of obturator 404. Tip 439 is configured to perform blunt dissection in subcutaneous tissue 202 of the patient. Tip 439 may have any shape that enables obturator 404 to function as described herein. Obturator 404 may be fabricated from, for example, polycarbonate, polysulfone, or another similarly resilient material.

A method of implanting ICM 100 using injection system 400 will now be described with respect to FIGS. 4A-4D. An incision (e.g., a 6 millimeter (mm) incision) is made in the patient using, for example, a surgical scalpel. With obturator 404 inserted into injector housing 402 and ICM 100 inserted into receptacle 420, injector housing first end 410 is inserted through the incision into the patient's tissue. As shown in FIG. 4B, tip 439 extends beyond first end 410 and provides a relatively small spear-shaped entry point into the tissue. At this point, tip 439 is used to perform blunt dissection in subcutaneous tissue of the patient, in preparation for the deployment of ICM 100. To form a cylindrical channel for ICM 100 below the patient's skin, the injector housing may be advanced until receptacle 420 reaches the incision.

Once blunt dissection is completed, as shown in FIGS. 4C and 4D, obturator 404 is pulled back partially out of injector housing 402 in a first direction (i.e., towards injector housing second end 412), as shown in FIG. 4B. Once tip 439 passes ICM 100 and receptacle 420, ICM 100 drops (i.e., due to gravity) from receptacle 420 into second tube portion 416.

Figure 5:
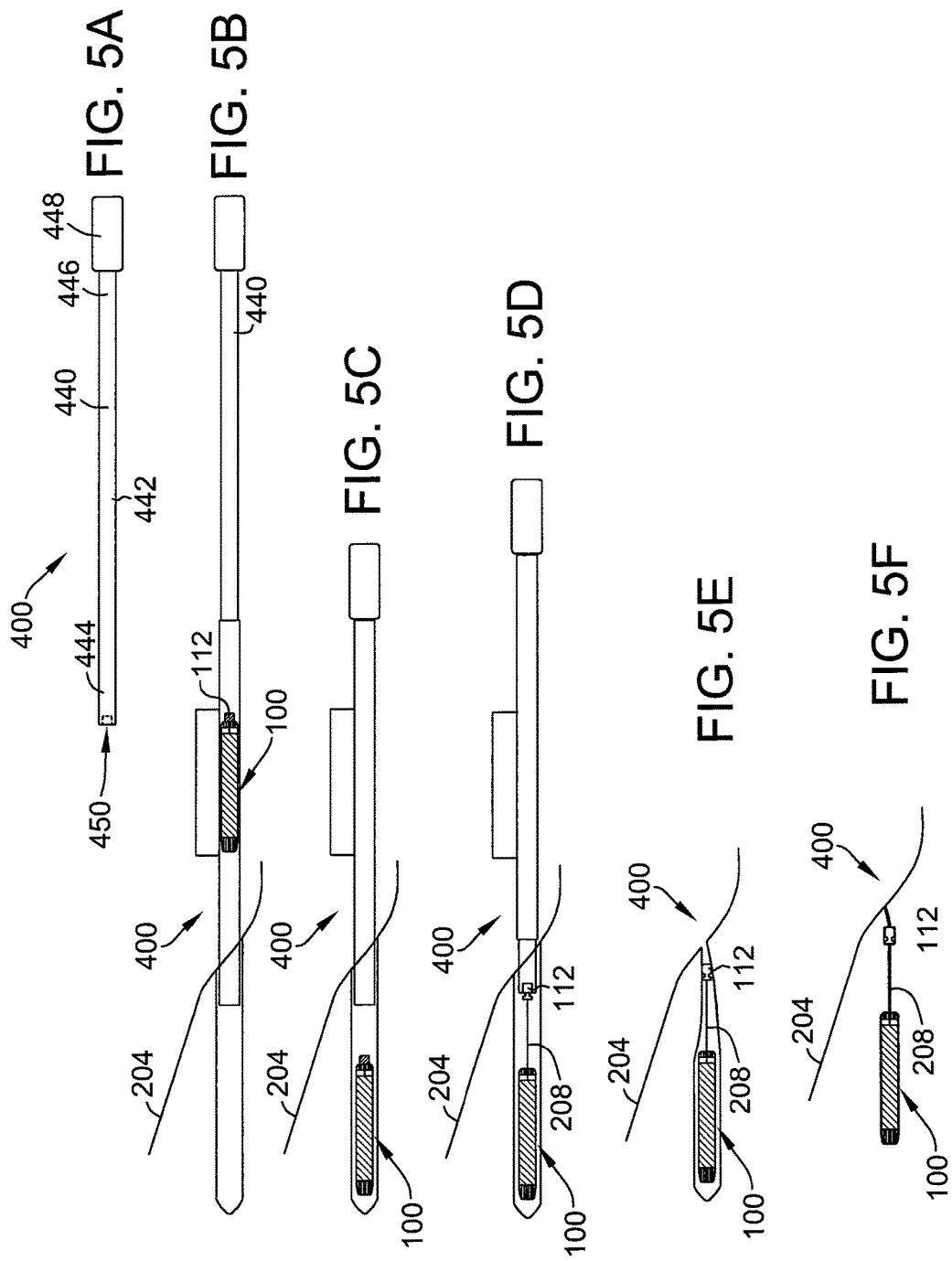
FIGS. 5A-5F are schematic diagrams illustrating operation of one embodiment of a system for implanting the ICM shown in FIG. 1.

FIGS. 5A-5F are schematic diagrams illustrating operation of system 400 to finalize the implant process. As shown in FIG. 5A, system 400 includes a pushing tool 440 including a substantially cylindrical shaft 442 that extends from a first end 444 to proximate a second end 446. A handle 448 is formed at second end 446 of pushing tool 440. Handle 448 has a diameter that is larger than the diameter of cylindrical shaft 442 and the inner diameter of second tube portion 416. A cup-shaped recess 450 is formed in first end 444. Recess 450 is configured to surround and engage marker 112 (e.g., in a snap-fit engagement).

As shown in FIG. 5B, after ICM 100 has dropped into second tube portion 416, pushing tool 440 is inserted into second tube portion 416 such that recess 450 engages marker 112. Notably, injector housing 402 has been pulled back from tissue 202 to allow ICM 100 to be inserted into the channel formed by obturator 404 by advancing pushing tool 440, as shown in FIG. 5C.

As shown in FIG. 5D, once ICM 100 is deposited in tissue 202, pushing tool 440 and marker 112 are retracted, disengaging marker 112 from proximal pickup electrode 102 and exposing suture 208. By applying a small force to pushing tool 440, marker 112 may be disengaged from pushing tool 440 such that marker 112 remains in tissue 202, relatively close to the surface of skin 204, as shown in FIG. 5E. In the event that marker 112 actually exits the skin insertion site, the person performing the implantation procedure may simply wrap any excess length of suture 208 around bobbin portion 306. FIG. 5E illustrates the final implantation position of ICM 100 once the insertion site has been closed (e.g., using tissue adhesive).

Figure 6:
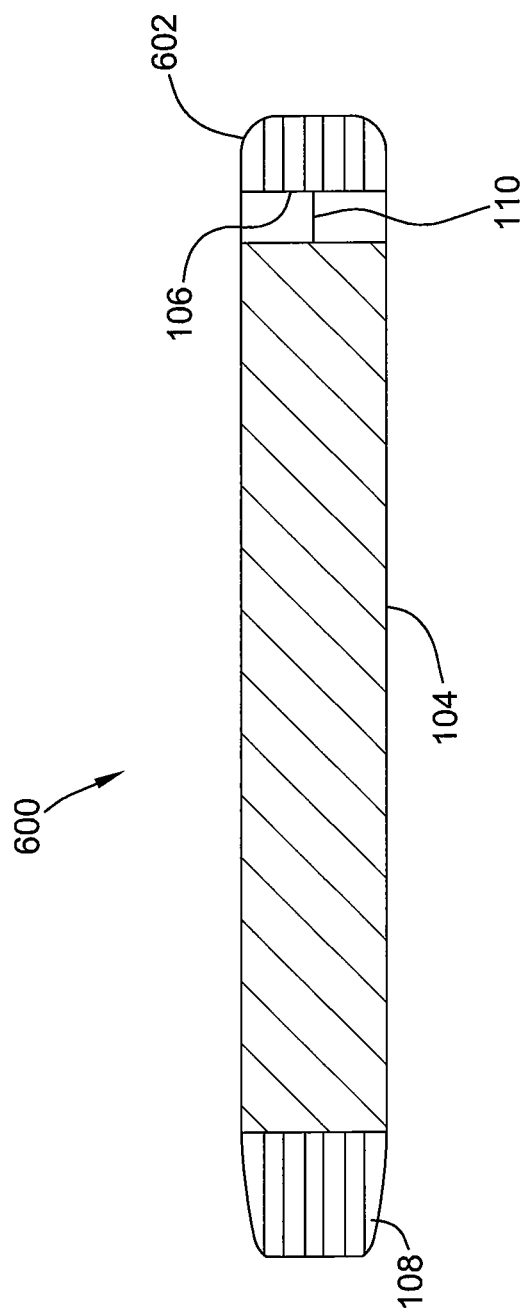
FIG. 6 is a schematic diagram of an alternative embodiment of an ICM.

FIG. 6 is a schematic diagram of an alternative embodiment of an ICM 600. Unless otherwise noted, ICM 600 is substantially similar to ICM 100. As compared to ICM 100, instead of including a separate marker, ICM 600 includes a detectable material (e.g., a ferromagnetic material or a permanent magnet) in proximal pickup electrode 602. Accordingly, a metal detector or GMR sensor may be used to locate ICM 600 using techniques similar to those discussed above in relation to ICM 100.

Although the embodiments described herein discuss using a ferromagnetic material or permanent magnet as the detectable material, those of skill in the art will appreciate that other materials may also be used. For example, in one embodiment, suture 208 and/or marker 112 includes a fluorescent compound. If suture 208 and/or marker 112 is left near the surface of skin 204, a black light may be used to locate ICM 600, such that ICM 600 can be explanted as described herein. In other embodiments, the detectable material may be a plastic material detectable by observing a change in dielectric properties or a change in conductivity while running a relatively current through the patient's skin. In still other embodiments, the ICM may include an antenna that broadcasts a detectable signal (e.g., in a medical implant communication service (MICS) band) to facilitate locating the ICM.

In yet another embodiment, suture 208 may be made of a conductive metal wire or cable, and may be connected through a feed through to a communication band (e.g., medical implant communication service (MICS) or Bluetooth) to act as an antenna to provide for enhanced communication capability. The same feedthrough or a second feedthrough may be used to provide for a connection. For example, the communication distance may be increased 10 to 100% or more. Accordingly, suture 208 may provide multiple functions, including functioning as an antenna for enhanced data communications, and functioning as a means for locating the implant for explantation. For example, using a receiver to sweep in proximity of the implanted device, the explanter can use signal strength to precisely locate the implant site. Suture 208 may be used to pull and extract the device from tissue at explant. Notably, an ICM antenna is typically embedded in epoxy 106 adjacent to proximal pickup electrode 102. However, this is a relatively confined location. Accordingly, using suture 208 as the ICM antenna can increase the antenna size and thus enhance communication abilities.

Further, in some embodiments, proximal pickup electrode 102 may be incorporated as part of marker 112. This provides a larger pickup dipole as compared to including proximal pickup electrode 102 as part of ICM 100, which increases the ECG signal and improves the performance of the ICM by increasing the signal to noise ratio. Suture 208 may incorporate two connective elements (i.e., one for the antenna and one for connection to the ECG electrode or ECG which is relatively low-frequency (e.g., 0.2 to 100 Hz) as compared to hundreds of KHz in to the GHz range for RF).

In embodiments where marker 112 includes a magnetic material, a magnetic tool (e.g., a magnetized hemostat) may be used. Further, in some embodiments, marker 112 includes a loop, or handle, that is engageable by a hemostat to facilitate retrieval.

The systems and methods described herein facilitate relatively straightforward locating and retrieval of an implanted device, such as an implantable cardiac monitor. The implanted device includes marker having a detectable material, such as a ferrous material or a permanent magnet that may be detected by an instrument. Once detected, an incision may be made proximate the marker, and the implanted device may be removed through the incision.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An implantable device comprising:
    a casing;
    a proximal pickup electrode coupled to the casing; and
    a marker disengageably coupled to the proximal pickup electrode in a snap-fit configuration, the marker is tethered to the proximal pickup electrode with a suture, wherein the marker includes a detectable material encased in a biocompatible material, and wherein the marker facilitates accurately locating and retrieving the implantable device after implantation in a patient.

2. The implantable device in accordance with claim 1, wherein the implantable device is an implantable cardiac monitor.

3. The implantable device in accordance with claim 1, wherein the marker comprises a bobbin portion defining a recess that is configured to receive the suture.

4. The implantable device in accordance with claim 1, wherein the detectable material is one of a ferrous material and a permanent magnet.

5. An implantation system comprising: an implantable device comprising:
    a casing;
    a proximal pickup electrode coupled to the casing; and
    a marker disengageably coupled to the proximal pickup electrode easing in a snap-fit configuration, the marker is tethered to the proximal pickup electrode with a suture, wherein the marker includes a detectable material encased in a biocompatible material, and wherein the marker facilitates accurately locating and retrieving the implantable device after Implantation in a patient; and
    an insertion tool configured to implant the implantable device in the patient.

6. The implantation system in accordance with claim 5, wherein the insertion tool comprises a pushing tool configured to insert the implantable device into tissue of the patient, the pushing tool having a cup-shaped recess configured to engage the marker.

7. The implantation system in accordance with claim 5, wherein the insertion tool comprises on obturator configured to create a channel for receiving the implantable device in tissue of the patient.

8. The implantation system in accordance with claim 5, further comprising a detection device configured to locate the marker once the implantable device is implanted.

9. The implantation system in accordance with claim 8, wherein the detection device comprises one of a metal detector and a giant magnetoresistance sensor.

10. The implantation system in accordance with claim 5, wherein the implantable device is an implantable cardiac monitor.

11. The implantation system in accordance with claim 10, wherein the suture made of a conductive material such that the suture is configured to function as an antenna.

12. The implantation system in accordance with claim 5, wherein the detectable material is one of a ferrous material and a permanent magnet.

13. The implantable device in accordance with claim 1, wherein the detectable material comprises a fluorescent compound.

14. The implantable device in accordance with claim 1, wherein the detectable material comprises a plastic material detectable by observing a change in dielectric properties when a current is applied to the patient's skin.

15. The implantation system in accordance with claim 5, wherein the detectable material comprises a fluorescent compound.

16. The implantation system in accordance with claim 5, wherein the detectable material comprises a plastic material detectable by observing a change in dielectric properties when a current is applied to the patient's skin.

* * * * *